US008815411B2

(12) United States Patent
Forrest et al.

(10) Patent No.: US 8,815,411 B2
(45) Date of Patent: Aug. 26, 2014

(54) STABLE BLUE PHOSPHORESCENT ORGANIC LIGHT EMITTING DEVICES

(75) Inventors: Stephen R. Forrest, Ann Arbor, MI (US); Mark Thompson, Anaheim, CA (US); Noel Giebink, Ann Arbor, MI (US)

(73) Assignees: The Regents of the University of Michigan, Ann Arbor, MI (US); University of Southern California, Los Angeles, CA (US)

( * ) Notice: Subject to any disclaimer, the term of this patent is extended or adjusted under 35 U.S.C. 154(b) by 1029 days.

(21) Appl. No.: 12/257,638

(22) Filed: Oct. 24, 2008

(65) Prior Publication Data

US 2009/0278444 A1 Nov. 12, 2009

Related U.S. Application Data

(60) Provisional application No. 60/986,804, filed on Nov. 9, 2007.

(51) Int. Cl.
*H01L 51/54* (2006.01)
*C09K 11/06* (2006.01)
*H01L 51/50* (2006.01)
*H01L 51/00* (2006.01)
*C07F 15/00* (2006.01)

(52) U.S. Cl.
CPC ........ *H01L 51/5016* (2013.01); *H01L 51/0084* (2013.01); *C07F 15/0033* (2013.01); *C09K 11/06* (2013.01); *C09K 2211/1059* (2013.01); *C09K 2211/185* (2013.01); *Y10S 428/917* (2013.01)
USPC ........... 428/690; 428/917; 313/504; 313/506; 252/301.16; 257/40; 257/102; 257/E51.044; 548/108

(58) Field of Classification Search
CPC ........ C09K 11/06; C09K 2211/182–2211/188; C09K 2211/1059; H01L 51/5016; H01L 51/0083–51/0089; C07F 15/0006; C07F 15/002; C07F 15/0033; C07F 15/0046; C07F 15/0073; C07F 15/0086; C07F 15/04; C07F 15/06

See application file for complete search history.

(56) References Cited

U.S. PATENT DOCUMENTS

| 4,769,292 A | 9/1988 | Tang et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 5,925,980 A | 7/1999 | So et al. |
| 5,932,895 A | 8/1999 | Shen et al. |
| 5,949,187 A | 9/1999 | Xu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,133,692 A | 10/2000 | Xu et al. |
| 6,194,089 B1 | 2/2001 | Choong et al. |
| 6,294,398 B1 | 9/2001 | Kim et al. |
| 6,303,238 B1 | 10/2001 | Thompson et al. |
| 6,326,224 B1 | 12/2001 | Xu et al. |
| 6,337,102 B1 | 1/2002 | Forrest et al. |
| 6,468,819 B1 | 10/2002 | Kim et al. |
| 6,573,651 B2 | 6/2003 | Adachi et al. |
| 7,179,543 B2 | 2/2007 | Forrest et al. |
| 7,279,704 B2 | 10/2007 | Walters et al. |
| 2003/0230980 A1 | 12/2003 | Forrest et al. |
| 2004/0174116 A1 | 9/2004 | Lu et al. |
| 2005/0116622 A1* | 6/2005 | Lo et al. ........................ 313/504 |
| 2006/0006792 A1 | 1/2006 | Strip |
| 2006/0237715 A1 | 10/2006 | Park et al. |
| 2006/0251923 A1 | 11/2006 | Lin et al. |
| 2006/0287498 A1 | 12/2006 | Morishita |
| 2007/0003789 A1 | 1/2007 | Kwong et al. |
| 2007/0075631 A1 | 4/2007 | Tung et al. |
| 2007/0128466 A1* | 6/2007 | Nomura et al. ............... 428/690 |
| 2007/0190359 A1 | 8/2007 | Knowles et al. |

FOREIGN PATENT DOCUMENTS

| EP | 1154676 | 11/2001 |
| EP | 1450419 | 8/2004 |
| EP | 1722603 | 11/2006 |
| JP | 2007/262135 | 10/2007 |
| WO | WO 2004111066 | 12/2004 |
| WO | WO 2007/095118 | 8/2007 |
| WO | WO 2008/156879 | 12/2008 |

OTHER PUBLICATIONS

Baldo et al., "Highly Efficient Phosphorescent Emission from Organic Electroluminescent Devices," Nature, vol. 395, 151-154, 1998.

Baldo et al., "Very high-efficiency green organic light-emitting devices based on electrophosphorescence," Appl. Phys. Lett., vol. 75, No. 3, 4-6 (1999).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

(Continued)

*Primary Examiner* — Michael H Wilson
(74) *Attorney, Agent, or Firm* — Morgan, Lewis & Bockius LLP

(57) ABSTRACT

Novel combination of materials and device architectures for organic light emitting devices is provided. An organic light emitting device, is provided, having an anode, a cathode, and an emissive layer disposed between the anode and the cathode. The emissive layer includes a host and a phosphorescent emissive dopant having a peak emissive wavelength less than 500 nm, and a radiative phosphorescent lifetime less than 1 microsecond. Preferably, the phosphorescent emissive dopant includes a ligand having a carbazole group.

5 Claims, 10 Drawing Sheets

(56) References Cited

OTHER PUBLICATIONS

Wong, Wai-Yeung, "Multifunctional Iridium Complexes Based on Carbazole Modules as Highly Efficient Electrophosphors,"*Angew. Chem. Int. Ed.*, 45:7800-7803 (2006).

Sun et al. "Management of Singlet and Triplet Excitons for Efficient White Organic Light-Emitting Devices", Nature 20060413 GB, vol. 440, No. 7086, pp. 908-912, Apr. 12, 2006.

Bera R. N. et al. "Highly Branched Phosphorescent Dendrimers for Efficient Solution-Processed Organic Light-Emitting Diodes", Advanced Functional Materials, Wiley VCH, Weinheim, DE, No. 17, May 2007, pp. 1149-1152.

Bettington et al. "Tris-Cyclometalated Iridium (III) Complexes of Carbazole(fluorenyl)pyridine Ligands: Synthesis, Redox and Photophysical Properties, and Electrophosphorescent Light-Emitting Diodes", Chem. Eur. J. 2006, 00, 0-0; full paper.

Hobson P. A. et al., "Surface plasmon mediated emission from organic light-emitting diodes" Advanced Materials, Wiley VCH, Weinheim, Germany, vol. 14, No. 19, Oct. 2002, pp. 1393-1396.

Peng et al., "Efficient organic light-emitting diode using semitransparent silver as anode" Applied Physics Letters 87, 173505, p. 1-3 (2005).

Clymer et al. "Characterization of thin-metal anode buffers in organic devices" Microwave and Optical Technology Letters, vol. 48, No. 10, Oct. 2006, pp. 2070-2072.

Peng et al. "Efficiency improvement of phosphorescent organic light-emitting diodes using semitransparent Ag as anode" Applied Physics Letters, vol. 88, No. 3, 2006. p. 1-3; 033509.

Lin Ke; Burden et al., "Au-ITO Anode for efficient polymer light-emitting device operation" IEEE Photonics Technology Letters, vol. 17, No. 3, Mar. 2005, pp. 543-545.

Moon Jong-Min et al. "Enhancement of hole injection using ozone treated Ag nanodots dispersed on indium tin oxide anode for organic light emitting diodes" Applied Physics Letters, AIP, American Institute of Physics, NY, vol. 90, No. 16, Apr. 20, 2007, pp. 163516-163516, XP012094284.

Kondakov et al., "Free-radical Pathways in Operational Degradation of OLEDs", Journal of SID 16/1, 2008, pp. 37-44.

Lo et al., "Blue Phosphorescence from Iridium(III) Complexes at Room Temperature", Chem. Mater. 2006, 18, pp. 5119-5129.

Kondakov et al., "Distinguished Paper: Structural Identification of Chemical Products and Mechanism of Operational Degradation of OLEDs", SID 07 Digest, pp. 1494-1496, 2007.

Giebink et al., "Intrinsic Luminance loss in Phosphorescent Small-Molecule Organic Light Emitting Devices Due to Bimolecular Annihilation Reactions", Journal of Applied Physics, vol. 103, Issue 4, pp. 044509-044509-9 (2008).

Reineke et al., "Triple-Exciton Quenching in Organic Phosphorescent Light-Emitting Diodes with Ir-based Emitters", Physical Review B 75, 2007, pp. 125328.

Yates et al., "Surface Plasmon-Polariton Mediated Emission from Phosphorescent Dendrimer Light-Emitting Diodes", Applied Physics Letters, v. 88, 2006, pp. 161105.

Baldo et al., "Transient Analysis of Organic Electrophosphorescence. II. Transient Analysis of Triplet-Triplet Annihilation", Physical Review B, V. 62, No. 16, 2000, pp. 10967-10977.

Kozlov et al., "Optical Properties of Molecular Organic Semiconductor Thin Films Under Intense Electrical Excitation", Applied Physics Letters, v. 74, No. 8, 1999, pp. 1057-1059.

Holmes et al., "Efficient, Deep-Blue Organic Electrophosphorescence by Guest Charge Trapping", Applied Physics Letters, V. 83, No. 18, 2003, pp. 3818-3820.

Pardo et al., "In Situ Purification of Organic Materials for Organic Light-Emitting Device Fabrication", Japanese Journal of Applied Physics, Part 1, V. 40, No. 8, 2001, pp. 4922-4923.

Chang et al., "Graded Doping Profiles for Reduction of Carrier Trapping in Organic Light-Emitting Devices Incorporating Doped Polymers", Appl. Phys. Lett. vol. 78, No. 5, 2001, pp. 574-576.

Meyer et al. "Highly Efficient Simplified Organic Light Emitting Diodes", Appl. Phys. Lett. vol. 91, 2007, p. 113506.

Kiy et al., "Observation of the Mott-Gurney Law in Tris(8-hydroxyquinoline) Aluminum Films", Appl. Phys. Lett. vol. 80, No. 7, 2002, pp. 1198-1200.

Salvatore Cina, "Recent Development in Organic Light Emitting Diodes (OLEDs)", CDT, Greenwich House, pp. 1-27, Mar. 2002.

Popovic et al., "Reliability and Degradation of Small Molecule-Based Organic Light-Emitting Devices (OLEDs)", IEEE Journal on Selected Topics in Quantum Electronics, vol. 8, No. 2, 2002, pp. 362-371.

Tutis et al., "The Mechanism of Lifetime Extension Due to CuPc Injection Layer in Organic Light Emitting Diodes", Proc. of SPIE vol. 5464, pp. 330-336, 2004.

Low et al., "Photo and Photo-Oxidative Degradations of Poly(phenylene vinylene) Derivatives", Thin Solid Films 413, 2002, 160-166, 2002.

Freeman et al., "Color II, and CFA Interpolation", Mit EECS 6.098/6.882, 2006.

International Search Report and Written Opinion corresponding to the PCT/US2008/082647 application dated Jul. 6, 2009.

International Search Report and Written Opinion corresponding to the PCT/US2008/082328 application dated Mar. 10, 2009.

International Search Report/Written Opinion corresponding to PCT/US2008/082640 application, Jun. 11, 2008.

U.S. Appl. No. 10/233,470, filed Sep. 4, 2002.

* cited by examiner

STABLE BLUE PHOSPHORESCENT ORGANIC LIGHT EMITTING DEVICES

This application claims priority to U.S. Provisional Application Ser. No. 60/986,804 filed Nov. 9, 2007, the disclosures of which are herein expressly incorporated by reference in their entirety.

This invention was made with government support under DE-FC26-04NT42272, awarded by the U.S. Department of Energy. The government has certain rights in the invention.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

BACKGROUND

1. Field of the Invention

The invention relates generally relates to organic light emitting devices (OLEDs). More specifically, the invention is directed to OLEDs having long lifetimes, including blue devices.

2. Related Art

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure of Formula I:

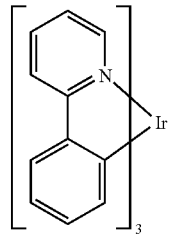

In this, and later figures herein, the dative bond from nitrogen to metal (here, Ir) as a straight line is depicted.

The limited operational stability of organic light emitting devices (OLEDs), however, presents a challenge to their wide-spread acceptance for use in large-area displays and solid-state lighting. While improved packaging techniques and material purity have lead to significant progress in eliminating extrinsic sources of degradation, the remaining intrinsic luminance loss and voltage rise accompanying long term device operation are not yet well understood.

Various hypotheses have been offered to explain the basis for intrinsic degradation in device efficiency, with the most widely accepted advocating chemical degradation of a fraction of the emissive constituent molecules. Presumably, bond cleavage produces radical fragments, which then participate in further radical addition reactions to form even more degradation products. These products act as non-radiative recombination centers, luminescence quenchers, and deep charge traps. For example, several studies have shown that both anions and cations of tris(8-hydroxyquinoline) aluminum (Alq$_3$) are unstable, and evidence has recently been presented that the excited states themselves may form reaction centers in the case of the common host material 4,4'-bis(9-carbazolyl)-2,2'-biphenyl (CBP).

SUMMARY OF THE INVENTION

Novel combination of materials and device architectures for organic light emitting devices is provided. An organic light emitting device, is provided, having an anode, a cathode, and an emissive layer disposed between the anode and the cathode. The emissive layer includes a host and a phosphorescent emissive dopant having a peak emissive wavelength less than 500 nm, and a radiative phosphorescent lifetime less than 1 microsecond. Preferably, the phosphorescent emissive dopant includes a ligand having a carbazole group.

BRIEF DESCRIPTION OF THE DRAWINGS

FIG. 4A shows the J-V characteristics of the devices studied. Inset: schematic of the device structure, with the dimensions, $x_1$-$x_3$ of FIG. 3, indicated as shown. FIG. 4B shows the external quantum efficiency (left scale) and emission spectrum (right scale) obtained at J=10 mA/cm$^2$.

FIG. 5A shows the luminance degradation versus time for initial brightnesses of $L_0$=1000, 2000, 3000, and 4000 cd/m$^2$ as indicated by the arrow. Solid black lines indicate a fit using the exciton localization degradation model discussed in the text. Note that the recombination zone width, $d_{rec}$, is variable in these fits. The data are reproduced for comparison with the exciton-exciton degradation model in FIG. 5B and with the exciton-polaron model in FIG. 5C. All fitting parameters are given in Table 1.

FIG. 6A shows the voltage rise for each of the four devices studied. The black lines are calculated using the exciton localization model. The data are reproduced in FIG. 6B and FIG. 6C for comparison with fits from the exciton-exciton and exciton-polaron models respectively. All fitting parameters are given in Table 1.

FIG. 7A shows the photoluminescence transients obtained for an as-grown device, one aged to $L(t')=0.59 L_O$ ($L_0=1000$ cd/m$^2$), and another aged to $L(t')=0.16 L_O$ of its initial $L_0=3000$ cd/m$^2$ brightness. Solid black lines are fits from the exciton localization model. Predictions of the exciton-exciton annihilation model are shown in FIG. 7B and those for the exciton-polaron annihilation model in FIG. 7C. Fitting parameters are given in Table 1.

In FIG. 8A, a direct or pre-dissociative potential, R, crosses the singlet or triplet first excited state energy surface. FIG. 8B shows the exciton-exciton annihilation process, which leads to a ground ($S_0$) and upper excited state ($S_n^*$ or $T_n^*$) according to the reaction $S_1(T_1)+S_1(T_1) \rightarrow S_0+S_n^*$ ($T_n^*$). Direct or pre-dissociation may occur from the upper excited state (gray arrow, route 1), or it may relax vibronically and undergo hot-molecule dissociation (gray arrow, route 2) as discussed in the specification. FIG. 8C shows the exciton-polaron mechanism, in which energy transfer from the exciton results in an excited polaron that dissociates along the analogous direct/pre-dissociative and hot-molecule routes. Dotted lines indicate vibrational energy levels within each an harmonic electronic manifold.

FIG. 9A shows the average defect density, $Q_{AVG}(t')$ and FIG. 9B shows the average defect formation rate, $F_X(t')$, per exciton, per hour, as defined in the text. The curves are calculated using the exciton-polaron model, at initial luminances of $L_0=1000$, 2000, 3000, and 4000 cd/m$^2$ as indicated by the arrow.

FIG. 10A shows the predicted lifetime improvement at $L_0=1000$ cd/m$^2$, obtained by increasing the recombination zone width, $d_{rec}$. FIG. 10B shows the increase in lifetime calculated for a reduction in degradation coefficient, $K_X$. Both FIGS. 10A and 10B assume the exciton-polaron model; the filled circles indicate where the devices of this study lie on the curves.

DETAILED DESCRIPTION

Definitions

Figure 1:
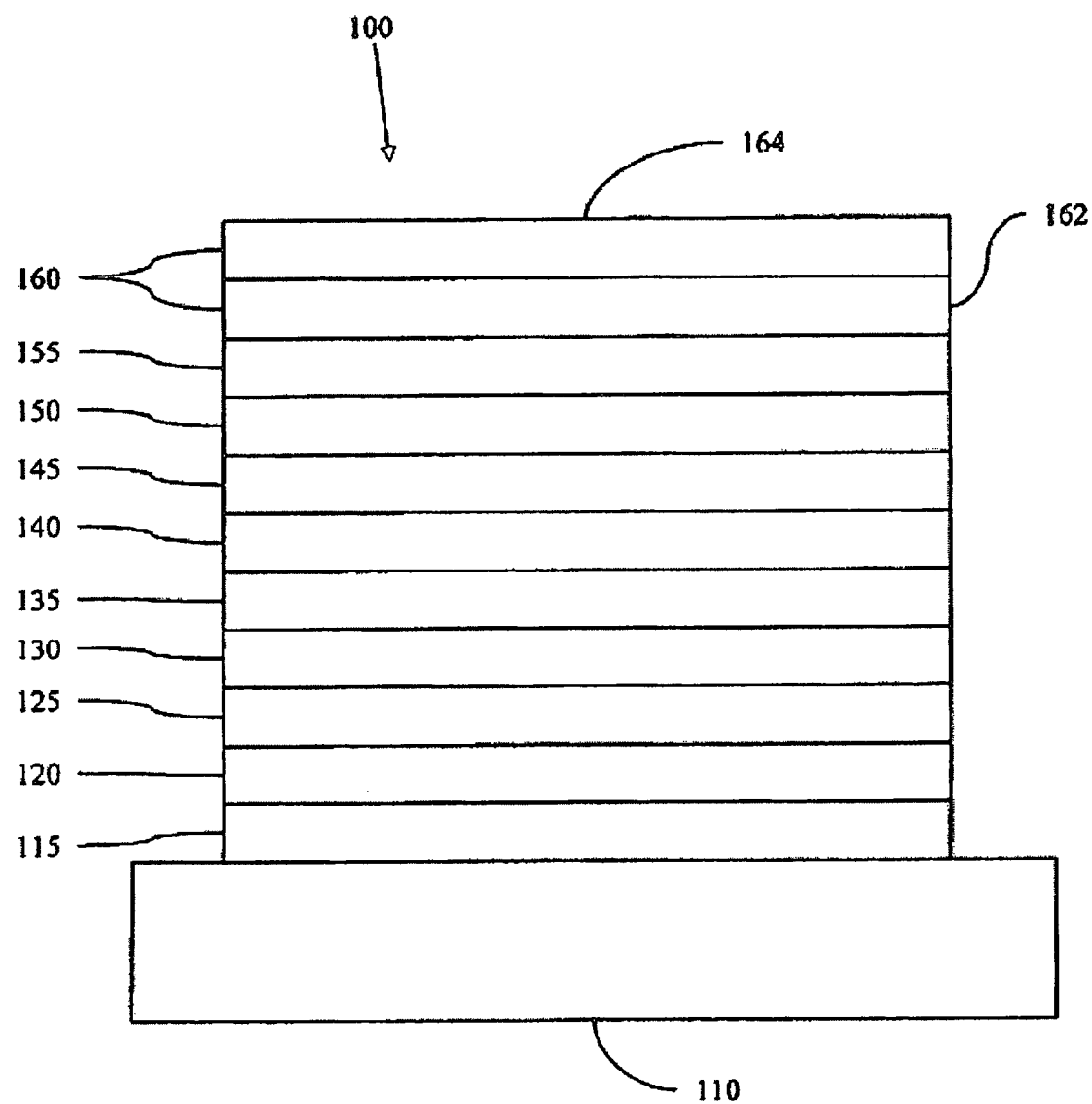
FIG. 1 shows an organic light emitting device having separate electron transport, hole transport, and emissive layers, as well as other layers.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand is referred to as "photoactive" when it is believed that the ligand contributes to the photoactive properties of an emissive material.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

More details on OLEDs, and the definitions described above, can be found in U.S. Pat. No. 7,279,704, which is incorporated herein by reference in its entirety.

Generally, an OLED may include at least one organic layer disposed between and electrically connected to an anode and a cathode. When a current is applied, the anode may inject holes and the cathode injects electrons into the organic layer(s). The injected holes and electrons each migrate toward the oppositely charged electrode. When an electron and hole localize on the same molecule, an "exciton," which is a localized electron-hole pair having an excited energy state, may be formed. Light may be emitted when the exciton relaxes via a photoemissive mechanism. In some cases, the exciton may be localized on an excimer or an exciplex. Non-radiative mechanisms, such as thermal relaxation, may also occur, but are generally considered undesirable.

Initially, OLEDs employed emissive molecules that emitted light from their singlet states ("fluorescence"). See, e.g., U.S. Pat. No. 4,769,292, which is incorporated by reference in its entirety. Fluorescent emission generally occurs in a time frame of less than about 10 nanoseconds. More recently, however, OLEDs having emissive materials that emit light from triplet states ("phosphorescence") have been demonstrated. See Baldo ET AL., "Highly Efficient Phosphorescent Emission from Organic Electroluminescent Devices," NATURE, vol. 395, 151-154, 1998; ("Baldo-I") and Baldo ET AL., "Very high-efficiency green organic light-emitting devices based on electrophosphorescence," APPL. PHYS. LETT., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

FIG. 1, which illustrates an embodiment, is a schematic showing an organic light emitting device 100. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 may be a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279, 704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$TCNQ at a molar ratio of about 50:1, as disclosed in U.S. Patent Application Publication No. 2003/0230980, which is incorporated by reference in its entirety. Examples of emissive and host materials are disclosed in U.S. Pat. No. 6,303,238, which is incorporated by reference in its entirety. An example of an n-doped electron transport layer is BPhen doped with Li at a molar ratio of about 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
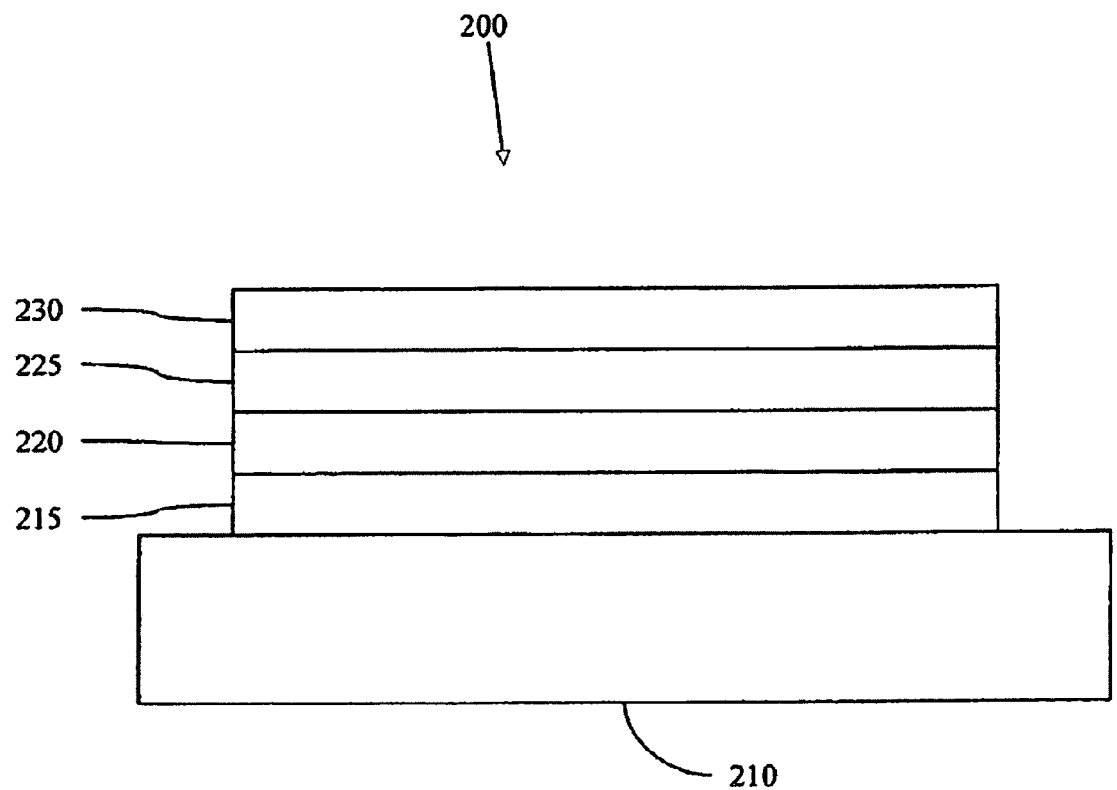
FIG. 2 shows an inverted organic light emitting device that does not have a separate electron transport layer.

FIG. 2, which illustrates another embodiment, shows an inverted OLED 200. The device may include a substrate 210, a cathode 215, an emissive layer 220, a hole transport layer 225, and an anode 230. Device 200 may be fabricated by depositing the layers described, in order. Since the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

In further embodiments, structures and materials not specifically described herein may also be used, such as OLEDs comprised of polymeric materials (PLEDs) such as disclosed in U.S. Pat. No. 5,247,190, which is incorporated by reference in its entirety. By way of further example, OLEDs having a single organic layer may be used. OLEDs may be stacked, for example as described in U.S. Pat. No. 5,707,745, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195, and/or a pit structure as described in U.S. Pat. No. 5,834,893, which are incorporated by reference in their entireties.

Unless otherwise specified, any of the layers of the various embodiments may be deposited by any suitable method. For the organic layers, particular methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102, which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes may be carried out in nitrogen or an inert atmosphere. For the other layers, particular methods include thermal evaporation. Specific patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods, however, may also be used.

The materials to be deposited may be modified to make them compatible with a particular deposition method. For example, substituents such as alkyl and aryl groups, branched or unbranched, and preferably containing at least about 3 carbons, may be used in small molecules to enhance their ability to undergo solution processing. Substituents having about 20 carbons or more may be used, and specifically in a range of about 3 to about 20 carbons may be used. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as a temperature in a range of about 18° C. to about 30° C., and more particularly at room temperature (about 20° C. to about 25° C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

Attaining long blue device lifetimes with phosphorescent emitters has been a long-standing problem in OLED device research. Suitable solutions to this problem would be useful for efficient, long-lived display devices as well as new white lighting applications. Notwithstanding many claims to improved lifetime materials and devices, device half-lives greater than about 2000 h starting from an initial luminance of about 500 nits have not been previously reported for phosphorescent blue devices with CIE color coordinates of X<0.17, Y<0.27. Accordingly, some aspects of the invention are generally directed to novel combination of materials and/ or device architectures, resulting in device half-lives greater than about 10,000 h at CIE coordinates 0.16, 0.26.

The modeling described herein provides a good match with experimental data. The model is based on bimolecular processes, such as exciton-exciton and exciton-polaron interaction, as a failure mechanism that create non-emissive reaction products. The model shows that undesirable exciton-polaron interaction are a strong function of both exciton energy and exciton lifetime. At higher energies and higher lifetimes, more undesirable interactions occur. Thus, blue emitters are the most problematic in the visible spectrum. One solution is to provide a blue emitter having a low radiative lifetime, i.e., a high radiative rate. As used herein, the "radiative lifetime" of a molecule is a material property that is a measure of the lifetime of an exciton on the molecule in the absence of any factors that might cause a non-radiative decay. The lifetime of an exciton in an actual device may be shorter than the radiative lifetime due to a variety of factors. Based on the modeling, the use of a blue phosphorescent emitter having a radiative lifetime less than 1 microsecond, corresponding to a radiative rate of $10^6$ per second, would lead to long-lived devices. Green and red devices can be long-lived with longer radiative lifetimes than blue, because the energy of the excitons is lower in the green and red devices.

Incorporating carbazole groups in place of phenyl may lower the lifetime of green emitting phosphorescent materials, without significantly altering color. This has been demonstrated for the following green emitting compounds:

Compound 1

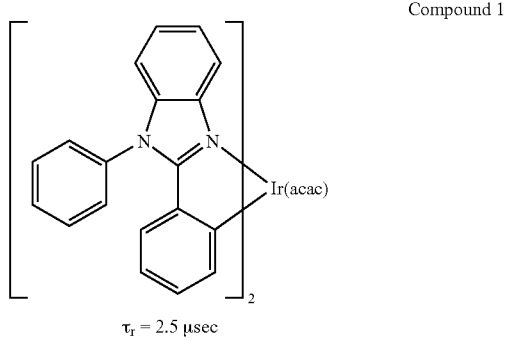

$\tau_r = 2.5 \ \mu sec$

Compound 2

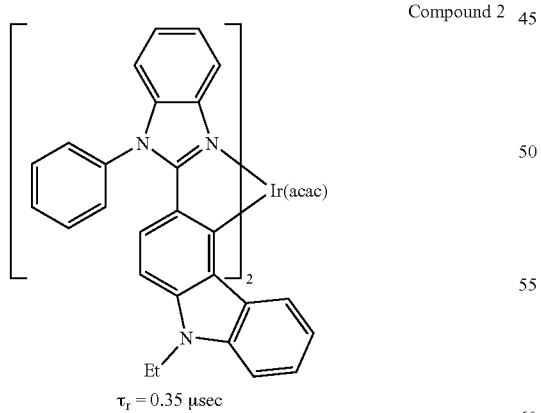

$\tau_r = 0.35 \ \mu sec$

See, Huang et. al, *Highly Phosphorescent Bis-Cyclometalated Iridium Complexes Containing Benzoimidazole-Based Ligands*, Chem. Mater. 2004, 16, 2480-2488. Specifically, the structures of Compounds 1 and 2 above are described in Huang at Chart 1, and the radiative lifetimes are provided in Table 1.

Compound 3

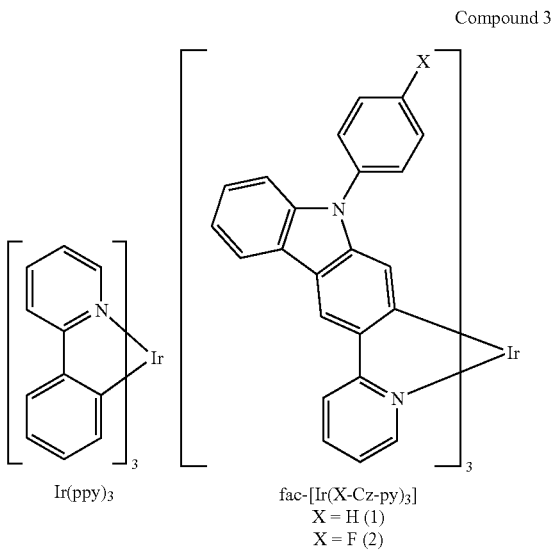

Ir(ppy)$_3$  fac-[Ir(X-Cz-py)$_3$]
X = H (1)
X = F (2)

See, Wong et. al, *Multifunctional Iridium Complexes Based on Carbazole Modules as Highly Efficient Electrophosphors*, Angewwandte Chemie International Ed. 2006, 45, 7800-7803. Specifically, Wong at page 2 shows a triplet radiative lifetime Compound 3 above of 1.07 microseconds, and indicates that the triplet radiative lifetime of Compound 3 is shorter than that of Ir(ppy)$_3$.

Applying a similar change to a blue emitter is expected to result in a similar decrease in radiative lifetime without significantly shifting color. Thus, blue phosphorescent emitters having short radiative lifetimes may be achieved by incorporating carbazoles into the imidazole containing blue dopants that are currently the best candidates for blue, i.e., by replacing phenyl-imidazolyl ligand with carbazolyl-imidazole ligands. Examples of such molecules include the following structures, possibly with ligands in addition to those illustrated:

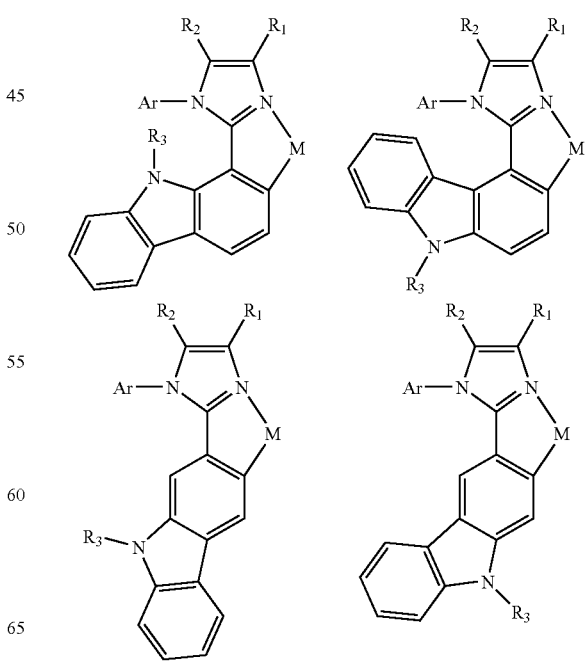

-continued

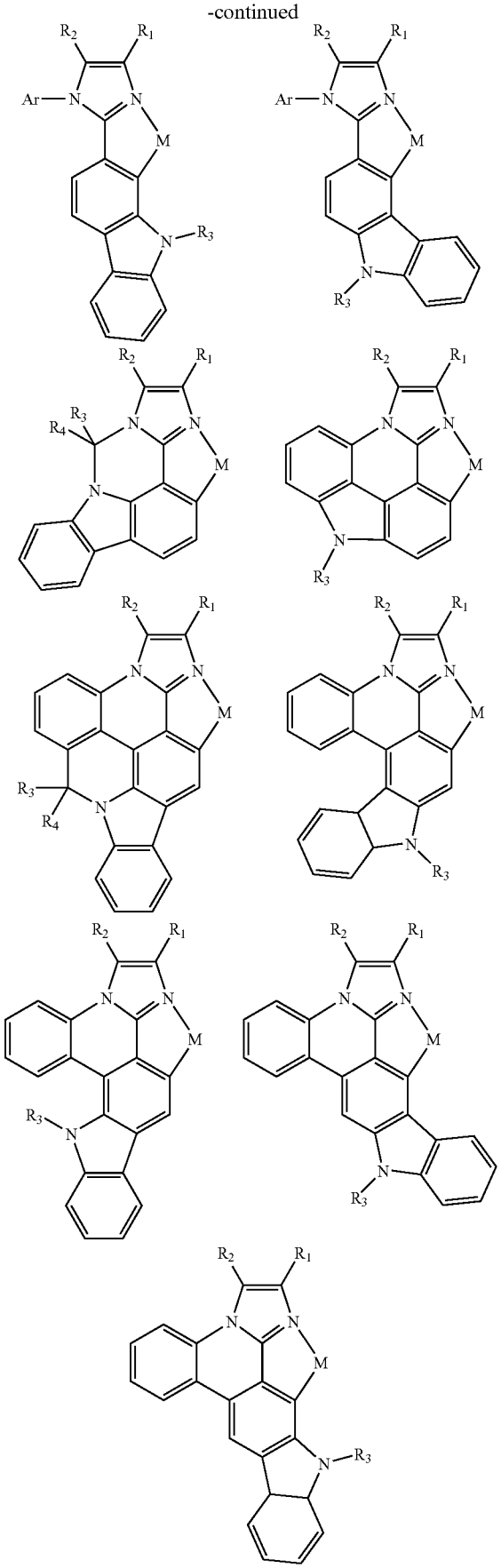

where $R_1$-$R_4$ are independently selected from the group consisting of: H, aryl and alkyl, where the aryl and alkyl may be further substituted, and where Ar is an aryl that may be further substituted. M is a metal having an atomic weight greater than 40. Preferably, M is iridium. As illustrated, the molecules show a single bidentate ligand coordinated to the metal M. Preferred molecules include any of the ligands illustrated coordinated to a metal. Where M has additional coordination sites, additional ligands may be coordinated to the metal. In a preferred group of molecules, M is iridium, which has 6 coordination sites (sufficient for 3 bidentate ligands), and all three ligands are the same.

In one aspect, the following ligands are coordinated to a metal to form a phosphorescent emissive molecule, which is incorporated into the emissive layer of an OLED:

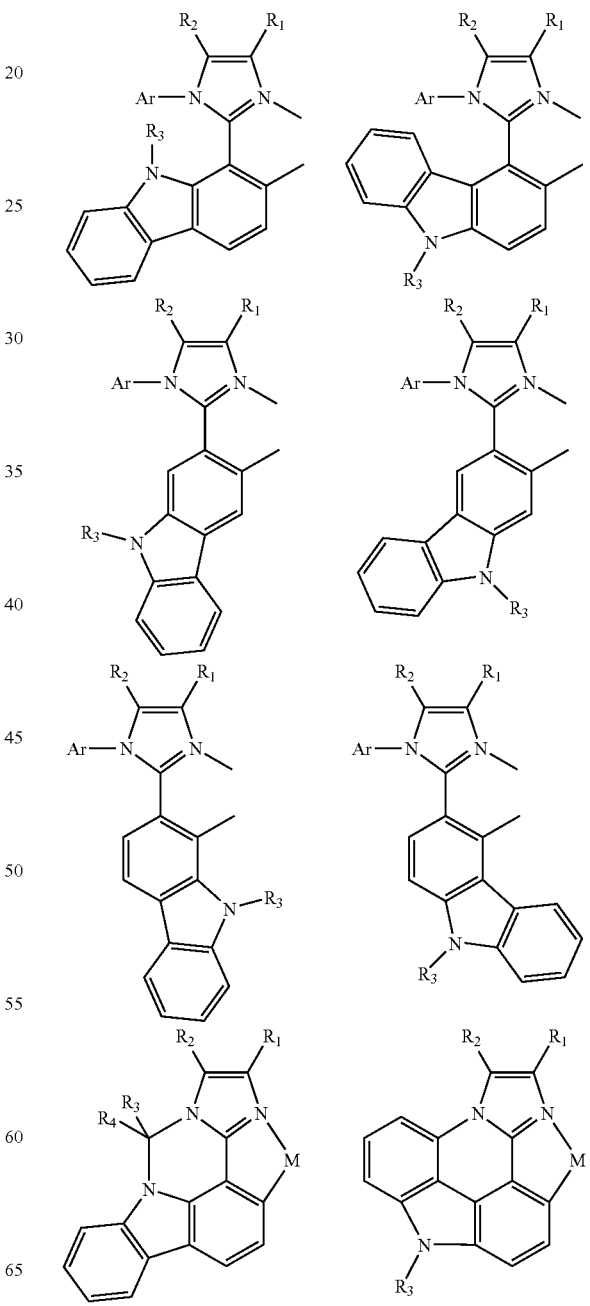

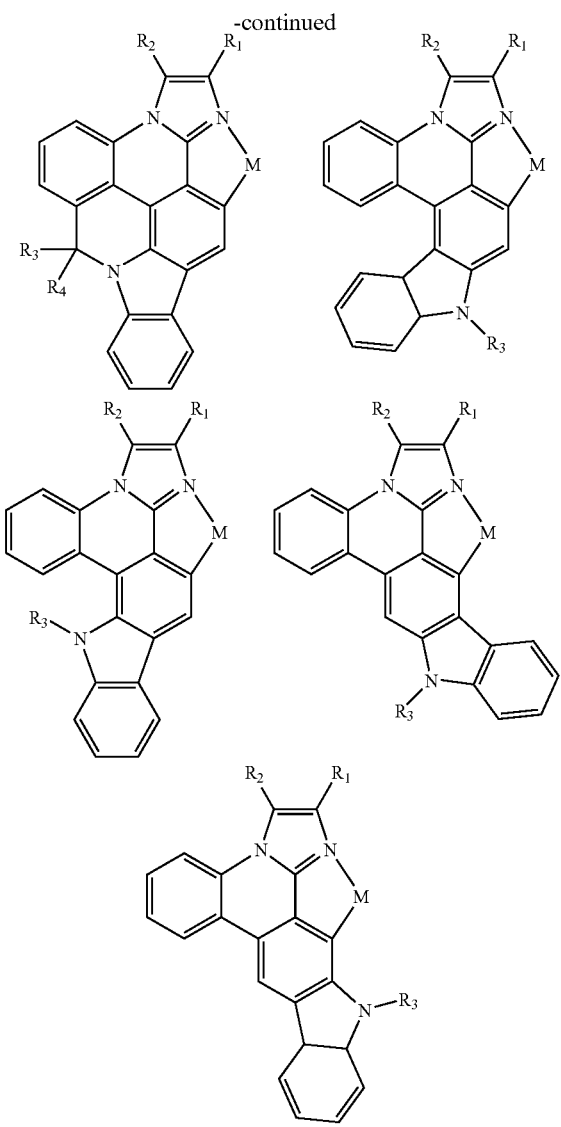

$R_1$-$R_4$ are independently selected from the group consisting of: H, aryl and alkyl, where the aryl and alkyl may be further substituted, and where Ar is an aryl that may be further substituted. The ligands may be coordinated to a metal M having an atomic weight greater than 40. Preferably, M is iridium. A molecule may include a plurality of the same ligand from the group above coordinated to a metal. For example, three identical ligands may be coordinated to an iridium atom. Different ligands may also be coordinated to the metal, so long as at least one of the ligands is selected from the group above.

It is also expected that rigid molecules have shorter lifetimes. The rigidity prevent the structure form "relaxing" in the excited state.

The model also shows that undesirable bimolecular interactions are also a function of exciton concentration. Reducing exciton concentration can therefore lead to longer lived devices. Exciton concentration can be reduced by spreading out the recombination zone. Such spreading can be achieved by several methods, including balancing the flow of charge carriers into the recombination zone, graded dopant concentrations, and using an emissive region including multiple slabs of material doped with emitter alternating with undoped regions.

Undesirable bimolecular interactions are also a function of the distance between an exciton on an emitter molecule, and any excitons or polarons on adjacent molecules. At larger distances, the rate of interaction between excitons and/or polarons is decreased. Introducing steric, bulky spacer groups onto the emitter molecule peripheries increases the distance between the exciton, localized on the emitter molecule inside the bulky spacer exterior, and excitons or polarons on surrounding molecules. Preferably, the added steric bulk does not affect emitter ground or excited states. Preferably, the size of a spacer group added to an emissive molecule is at least 10 angstroms, preferably 15 angstroms, and more preferably 20 angstroms. Spacer groups too large, above 50 angstroms, may have undesirable adverse effects on the conductivity of the emissive layer. It is desirable to design such spacer groups to minimize overlaps between the pi orbitals of the host and dopant. Aryl groups, alkanes, pyridines, azoles, and similar substituents are desirable. Dendrimers and alkane chains are also desirable. The use of such spacer groups is particularly desirable for phosphorescent emissive dopants having a peak emissive wavelength less than 500 nm.

The rate of undesirable bimolecular interactions is dependent on the concentration of excitons and polarons. Reducing these concentrations is one way to increase device lifetime. One way to reduce exciton concentration is to deliberately provide quenchers in the device, particularly in the emissive layer. Such quenchers could be designed in such a way that the quenching does not cause damage to the device. Such an approach may trade efficiency for lifetime, because some of the deliberately quenched excitons may have otherwise caused light emission.

Experimental and Modeling

According to one embodiment, the fundamental mechanisms leading to degradation during long term operation of a typical, blue electrophosphorescent OLED are provided. The trends in electrophosphorescence decay, voltage rise, and emissive layer photoluminescence quenching associated with electrical aging may be best fit to a model (infra) based on the assumption that defect sites generated during operation act as exciton quenchers, deep charge traps, and nonradiative recombination centers. Defect generation due to exciton-polaron annihilation interactions between the dopant and host molecules may lead to model predictions in good agreement with the data. Moreover, a link between guest exciton energy and to the annihilation induced defect formation rate may be suggested, with increasing guest emission energy leading to increased defect formation rates. Accordingly, the model may provide that the operational lifetime of blue OLEDs may be less than green and red due to the higher energy excitations of the former system. Finally, defect densities of about $10^{18}$ $cm^{-3}$ may result in greater than about 50% degradation from initial luminance.

Figure 3:
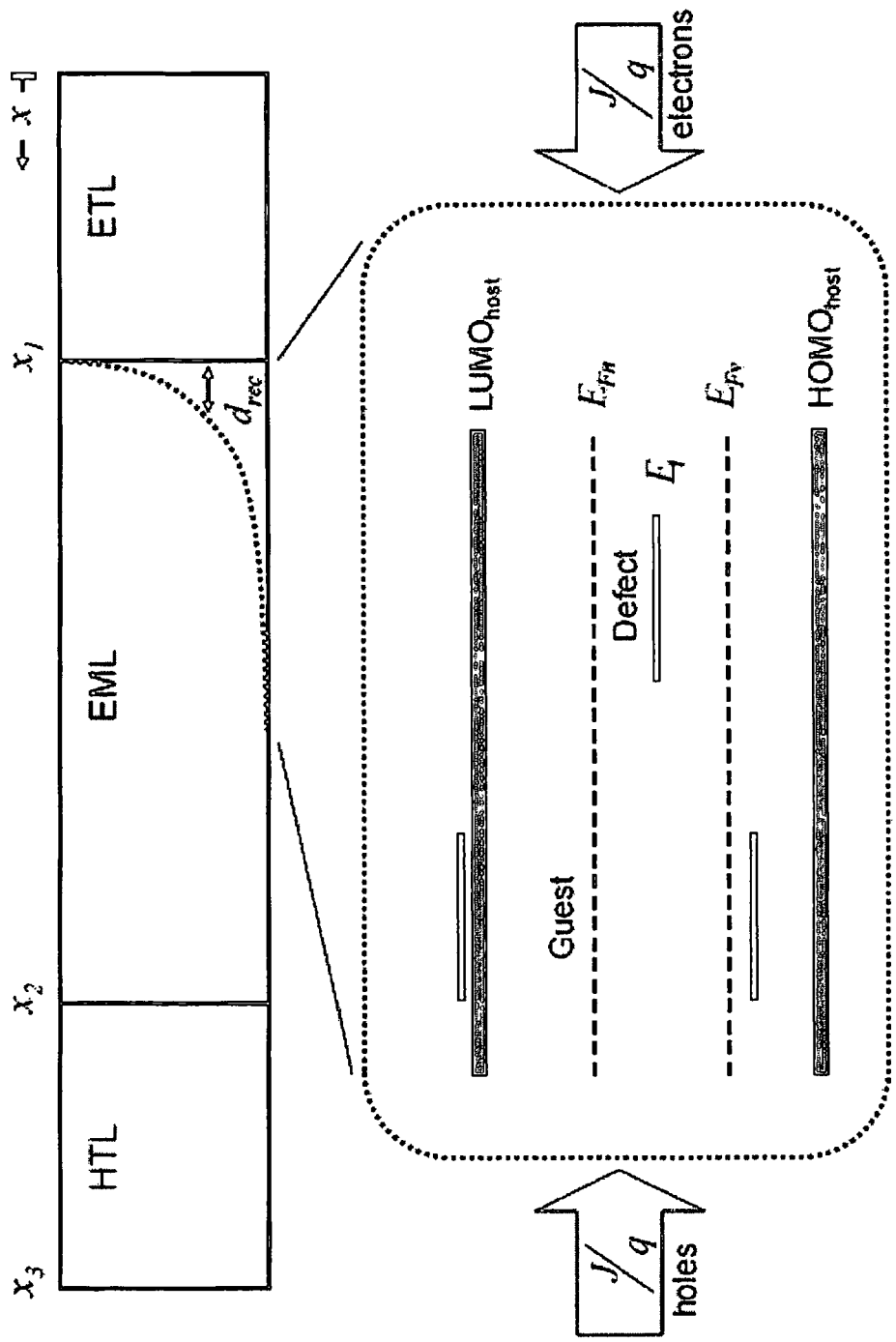
FIG. 3 provides a schematic of the model geometry and assumed energy level relationships. The recombination zone decays exponentially from the EML/ETL interface at $x_1$ with characteristic length, $d_{rec}$. Both phosphorescent guests and defects form deep traps within the host band-gap. The electron and hole quasi-Fermi levels under forward-bias are $E_{Fn}$ and $E_{Fv}$ respectively.
Figure 9:
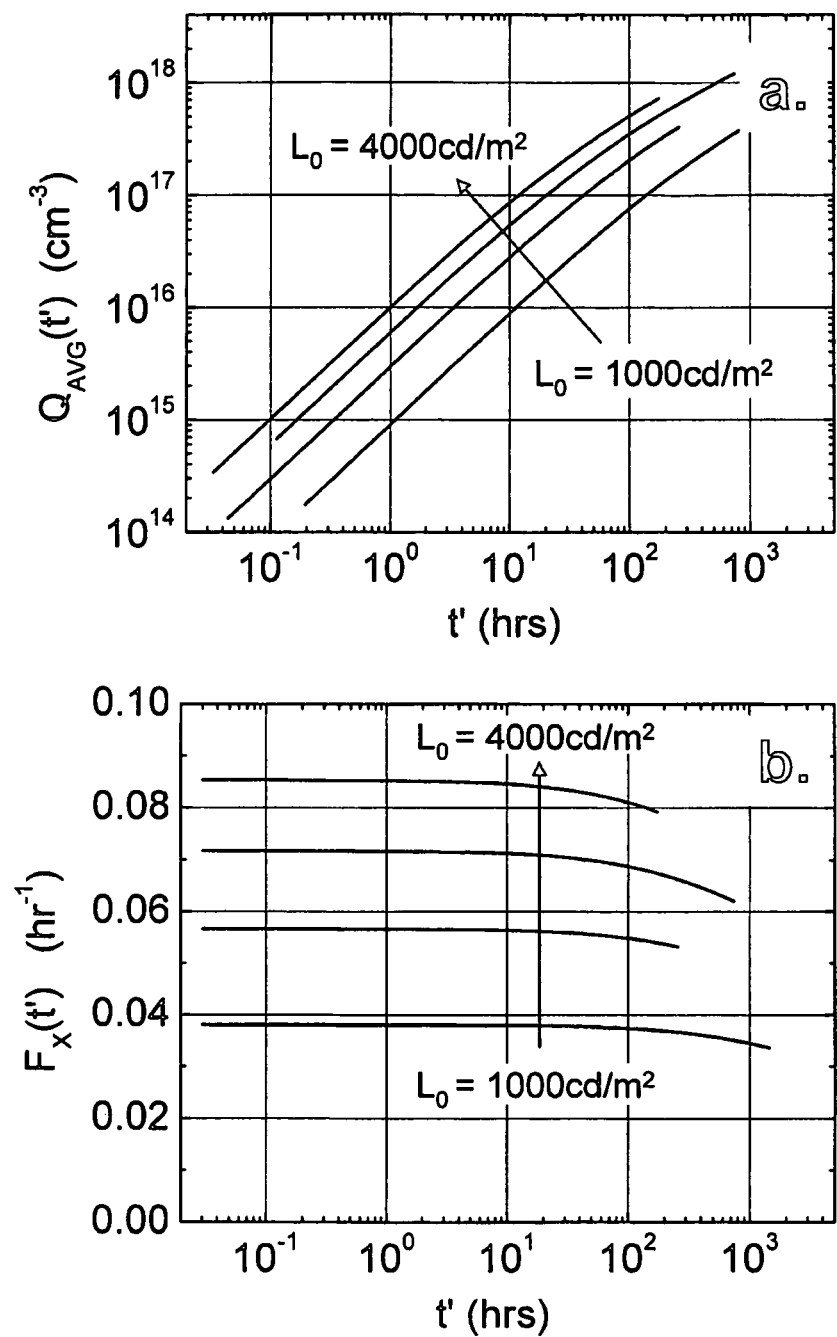
FIGS. 9A-9B.

Depending on their energy levels, defects may act as luminescent quenchers, non-radiative recombination centers, and deep charge traps. Luminance loss may result from the first two, while voltage rise, which has been linked to the presence of fixed space charge in the emissive region, may result from filling of the deep traps. This is depicted schematically in FIG. 9 for a single, discrete, deep defect state at energy, $E_t$, that lies between the highest occupied (HOMO) and lowest unoccupied molecular orbitals (LUMO) of the host. The energetics of the phosphorescent guest are also shown in FIG. 3. Thus, both defect and guest form discrete, deep hole traps that allow for direct exciton formation, although recombination is only radiative on the guest. Luminescence quenching by defects may occur if there exists an allowed transition resonant with that of the guest or host that enables Förster or Dexter energy transfer to occur.

Defects may be assumed to act only as hole traps, with $E_t$ representing the defect HOMO. In general, however, defects may have both their HOMO and LUMO, or a singly occupied molecular orbital within the host band gap, creating both electron and hole traps. In addition, the defect state itself may not lead directly to a quenching transition, but when occupied with a trapped charge, the resulting polaron might become a quenching center. The model presented below is general, however, and although it has been derived for the specific case shown in FIG. 3, it nevertheless remains applicable to these alternative scenarios, as discussed below.

According to one embodiment, a single recombination zone that may decay exponentially from one edge of the emissive layer (EML) with characteristic length $d_{rec}$, is depicted in FIG. 3. High efficiency electrophosphorescent OLEDs may have a charge balance factor near unity, hence it is assumed that equal numbers of electrons and holes enter the recombination zone. Excitons formed on the host may then rapidly transferred and localized on the phosphorescent guests as a result of their high doping concentration and host triplet energy. As a result, exciton diffusion out of the recombination zone may be negligible.

These considerations lead to rate equations for hole (p), electron (n), and exciton (N) densities in the recombination zone as follows:

$$\frac{dp(x,t,t')}{dt} = \frac{J}{qd_{rec}(1-\exp(-(x_2-x_1)/d_{rec}))}\exp(-(x-x_1)/d_{rec}) - \gamma n(x,t,t')p(x,t,t') - \sigma v_{th}[f_D(E_t)]Q(x,t')p(x,t,t') \quad [1]$$

$$\frac{dn(x,t,t')}{dt} = \frac{J}{qd_{rec}(1-\exp(-(x_2-x_1)/d_{rec}))}\exp(-(x-x_1)/d_{rec}) - \gamma n(x,t,t')p(x,t,t') - \gamma_2[1-f_D(E_t)]Q(x,t')p(x,t,t') \quad [2]$$

$$\frac{dN(x,t,t')}{dt} = \gamma n(x,t,t')p(x,t,t') - \left(\frac{1}{\tau} - K_{DR}Q(x,t')\right)N(x,t,t') \quad [3]$$

The electron, hole, and exciton densities may depend on the time scale of transport and energy level transitions, t (short), as well as on that of degradation, t' (long), due to formation of defects of density $Q(x,t')$. The electron and hole densities may be functions of the current density, J, the elementary charge q, and the device dimensions shown in FIG. 3. Excitons may be formed at the Langevin rate, $\gamma=q(\mu_n+\mu_p)/(\epsilon\epsilon_0)$, and decay with natural lifetime, $\tau$. The hole and electron mobilities in the doped emissive layer are $\mu_p$ and $\mu_n$, respectively, the relative dielectric constant of the emissive layer is $\epsilon \approx 3$, and $\epsilon_0$ is the permittivity of free space.

In Equation (1), holes with thermal velocity, $v_{th} \sim 10^7$ cm/s, trap at defect sites of energy, $E_t$, and cross section, $\sigma$. The Fermi factor, $f_D(E_t)=[\exp(E_t-E_{Fv})+1]^{-1}$, gives the probability that the hole trap is empty, where $E_{Fv}$ is the hole quasi-Fermi energy. Electrons in Equation (2) non-radiatively may recombine at a rate proportional to the trapped hole density, $Q(x,t')[1-f_D(E_t)]$, and the reduced Langevin coefficient, $\gamma_2=q(\mu_n)/(\epsilon\epsilon_0)$ since trapped holes are assumed to be immobile. Quenching of excitons by defects is described by the bimolecular rate coefficient, $K_{DR}$, in Equation (3). Note that only the constant prefactors change if defects trap electrons, or both carrier types, instead of only holes, as considered above.

The defect generation mechanism has four possible routes:

$$\frac{dQ(x,t')}{dt'} = \begin{cases} K_X n(x,t') \ K_X p(x,t') & [4a] \\ K_X N(x,t') & [4b] \\ K_X N^2(x,t') & [4c] \\ K_X N(x,t')n(x,t'), \ K_X N(x,t')p(x,t') & [4d] \end{cases}$$

where the rate constant, $K_X$, is consistent in dimension with the order of the reaction. In Equation (4a), the presence of an electron or hole (i.e. a polaron) leads to molecular degradation, while in Equation (4b) excitons are responsible. Defect formation is a product of exciton-exciton annihilation in Equation (4c), and of exciton-polaron (hole or electron) annihilation in Equation (4d).

On the short time scale, t, Equations (1)-(3) are at steady state and may be solved to yield an expression for $N(x,t')$. The resulting, coupled differential equations containing $N(x,t')$ and $Q(x,t')$ may then solved numerically. Thus, the normalized OLED luminescence as a function of time is:

$$EL_{norm}(t') = \frac{\int_{x_1}^{x_2} N(x,t')}{\int_{x_1}^{x_2} N(x,0)}, \quad [5]$$

and the defect formation rate per exciton, averaged over the recombination zone is:

$$F_X(t') = \frac{1}{d_{rec}} \int_{x_1}^{x_2} \frac{1}{N(x,t')} \frac{dQ(x,t')}{dt'} dx. \quad [6]$$

Here, the integration limits, $x_1$ and $x_2$, are defined in FIG. 3. The density of trapped charge increases with defect density following: $\rho_T(x,t')=qQ(x,t')[1-f_D(E_t)]$. Assuming that the growth of $\rho_T$ is offset by an equal density of opposing charge at the cathode, and that the free charge distributions under steady-state operation are not perturbed, then the voltage rise is given by:

$$\Delta V(t') \approx \int_0^{x_3} x\rho_T(x,t')dx. \quad [7]$$

The emissive layer photoluminescence (PL) transient will also be affected by defects. From Equation (3) at time, t', the PL intensity normalized to that at t=0 is:

$$PL_{norm}(t)|_{t'} = \frac{\int_{x_1}^{x_2} I_0(x)\exp[-(1/\tau + K_{DR}Q(x,t'))t]}{\int_{x_1}^{x_2} I_0(x)}. \quad [8]$$

Here, $I_0(x)$ is the intensity profile of the excitation pulse in the device emissive layer calculated by the transfer matrix method for the specific device structure, incident excitation angle, wavelength, and polarization considered.

EXAMPLES

Specific Example 1

Figure 4:
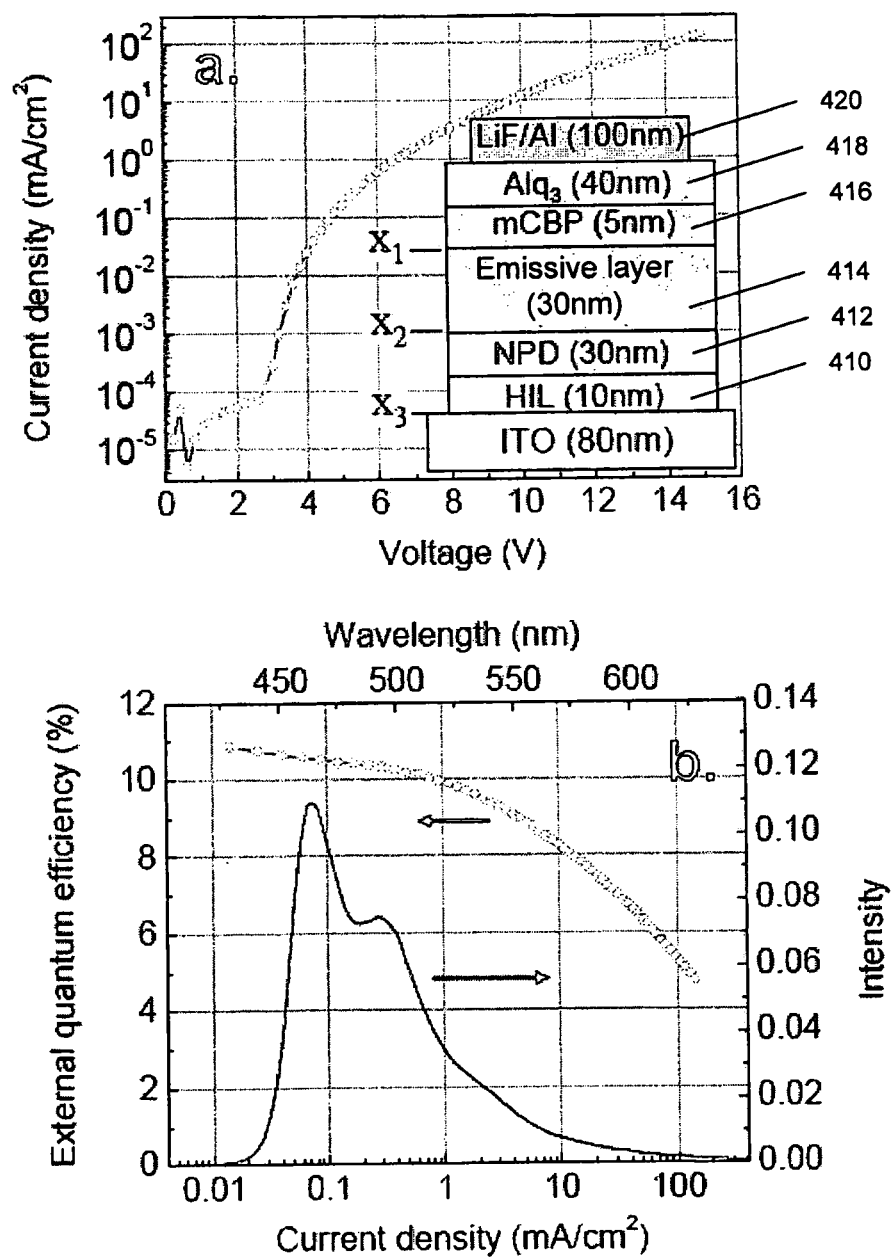
FIGS. 4A-4B.

Indium-tin-oxide (ITO) coated glass was cleaned with solvents and patterned into 2 mm² anode contact areas using standard photolithography techniques prior to organic film deposition. The ITO was oxygen plasma cleaned, exposed to UV-ozone treatment, and then loaded into a vacuum chamber with a base pressure of about $10^{-7}$ Torr. The device structure was as follows FIG. 4: a 10 nm thick hole injection layer 410, a 30 nm thick layer of the hole transporting 4,4'-bis[N-(1-naphthyl)-N-phenyl-amino]-biphenyl (NPD) 412, a 30 nm thick emissive layer 414 including mCBP doped with about 9 wt % of the blue phosphor fac-tris[3-(2,6-dimethylphenyl)-7-methylimidazo[1,2-f]phenanthridine] Iridium(III), and a 5 nm thick layer of mCBP 416 for exciton confinement within the EML. Electrons were injected into the EML through about a 40 nm thick layer of tris-(8-hydroxyquinoline) aluminum 418, capped by a cathode 420 including of about a 0.8 µm thick layer of LiF and about a 100 nm thick Al film. Following deposition, the OLEDs were transferred directly from vacuum into an oxygen and moisture-free $N_2$ glove box, and were subsequently encapsulated using a UV-curable epoxy, and a glass lid containing a moisture getter.

External quantum (EQE) and power efficiencies were calculated from the spectral intensity measured normal to the substrate using a SpectraScan PR705. The current and voltage measurements were obtained using a Keithley 236 source measurement unit. Operational lifetime measurements were performed at room temperature, and devices were aged at various constant currents while monitoring their operational voltage and light output. Photoluminescence transients were obtained periodically during electrical aging using a time-correlated single photon counting system from Horiba Jobin Yvon, with a wavelength of about $\lambda=335$ nm, pulsed excitation source incident at about 45° from normal. Photoluminescence from the emissive layer was obtained at a wavelength of about $\lambda=470$ nm to prevent collection of fluorescence from the transport layers.

The current density-voltage (J-V) characteristics and EQE for the OLEDs were plotted in FIGS. 4A and 4B, respectively. The device showed a peak forward viewing EQE=(11.0±0.2) %. The emission spectrum at J=10 mA/cm², with a peak at $\lambda=464$ nm, was due to the dopant and remained the same at all current densities, indicating that the recombination zone remained within the EML. The recombination was highest at the EML interface adjacent to the thin mCBP blocking layer 416. This conclusion was supported by the lack of NPD emission, and the fact that removal of the mCBP blocking layer resulted in significant $Alq_3$ emission.

FIG. 5A provided the normalized electrophosphorescence versus time for four different drive current densities: about 6.9, about 15.1, about 24.3 and about 34.4 mA/cm² corresponding to initial (t'=0) luminances of $L_O$=about 1000, about 2000, about 3000, and about 4000 cd/m², respectively. The operational lifetime, $LT_{80}$, corresponded to the time required for the luminance to degrade to $0.8L_O$. The rate of luminance loss increased monotonically with J; here lifetimes decreased from about 110 hrs at about 6.9 mA/cm², to about 9 hrs at about 34.4 mA/cm². The solid lines in FIG. 5A were derived from the model under the assumption that exciton localization on a dopant or host molecule led to defect formation (Equation 4b). The same experimental data were reproduced in FIGS. 5B and 5C to compare the model predictions for exciton-exciton annihilation (Equation 4c) and exciton-polaron (electron) annihilation (Equation 4d) defect formation processes, respectively.

The voltage rise corresponding to the luminance loss was plotted in each of FIGS. 6A-6C for comparison with each different modeling scenario. The solid lines of FIGS. 6A-6C were calculated using the same exciton localization, exciton-exciton, and exciton-polaron degradation models as in FIGS. 5A-5C.

FIGS. 7A-7C showed PL transients obtained from an as-grown device, a device degraded to a luminance at time t' of $L(t')=0.59 L_O$ ($L_O=1000$ cd/m²), and one degraded to $L(t')=0.16 L_O$ ($L_O=3000$ cd/m²). The predictions from each model were shown by solid lines in FIG. 7A (exciton localization), FIG. 7B (exciton-exciton annihilation), and FIG. 7C (exciton-polaron annihilation). The as-grown device exhibited a natural decay lifetime of $\tau=(1.10\pm0.08)\mu s$, while the degraded device transients became increasingly nonlinear, indicative of the existence of quenching. Fluorescence from NPD overlapping the $\lambda=470$ nm detection wavelength was responsible for the sharp decrease in intensity near t=0. The transients were normalized at the onset of phosphorescence, after the fluorescence had decayed to a negligible level (i.e., at about t>0.2 µs).

Figure 8:
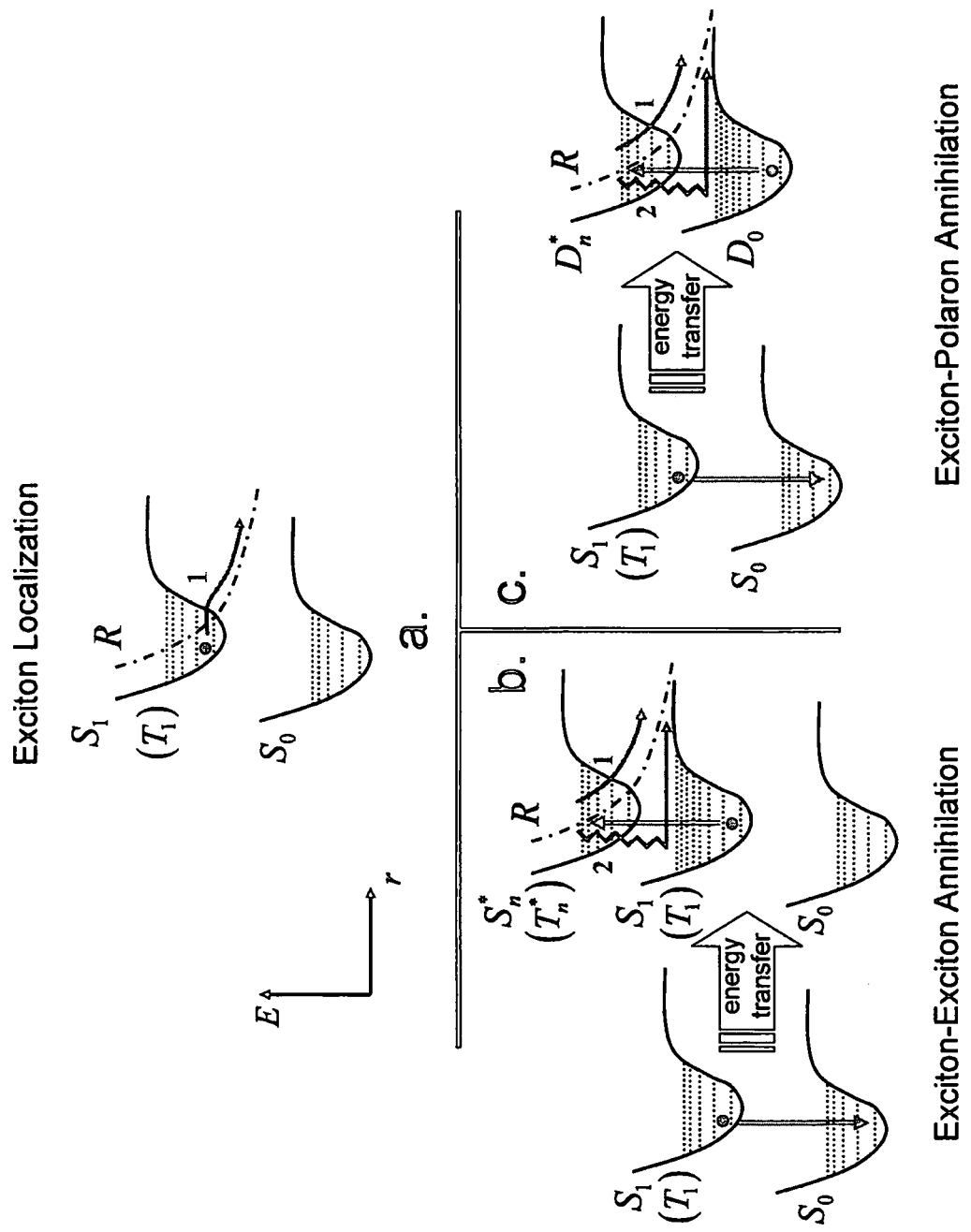
FIGS. 8A-8C is a configurational diagram showing the different dissociation mechanisms in terms of energy (E) and representative coordinate (r).

Configurational diagrams of the defect generation mechanisms proposed in Equation (4), were shown in FIG. 8. FIG. 8A shows the exciton localization pathway, where a direct or pre-dissociative potential, R, crossed the exciton energy surface. In FIG. 8B, annihilation of two singlet ($S_1$) or triplet ($T_1$) excitons yielded a ground state ($S_0$), and an upper excited state ($S_n^*$ or $T_n^*$), which were dissociated via a direct or pre-dissociative reaction (route 1) along R to yield radical fragments that resulted in defect states. Dissociation also occurred via the hot-molecule mechanism (route 2) if the upper excited state relaxed vibronically to create a hot first excited state. Similarly, FIG. 8C showed annihilation of an exciton ($S_1$ or $T_1$) and a polaron ($D_0$) to create a ground state ($S_0$) and an excited polaron ($D_n^*$), which dissociated along route 1 or 2, analogous to the previous case above.

Figure 5:
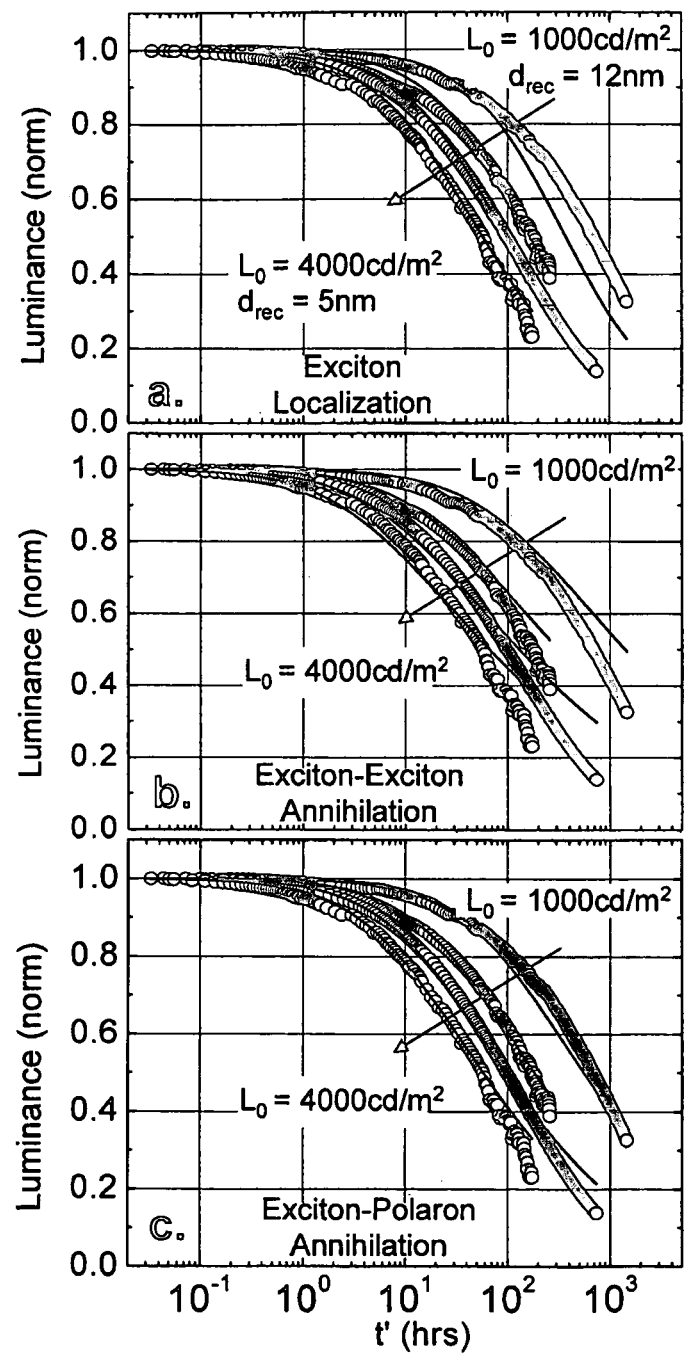
FIGS. 5A-5C.
Figure 6:
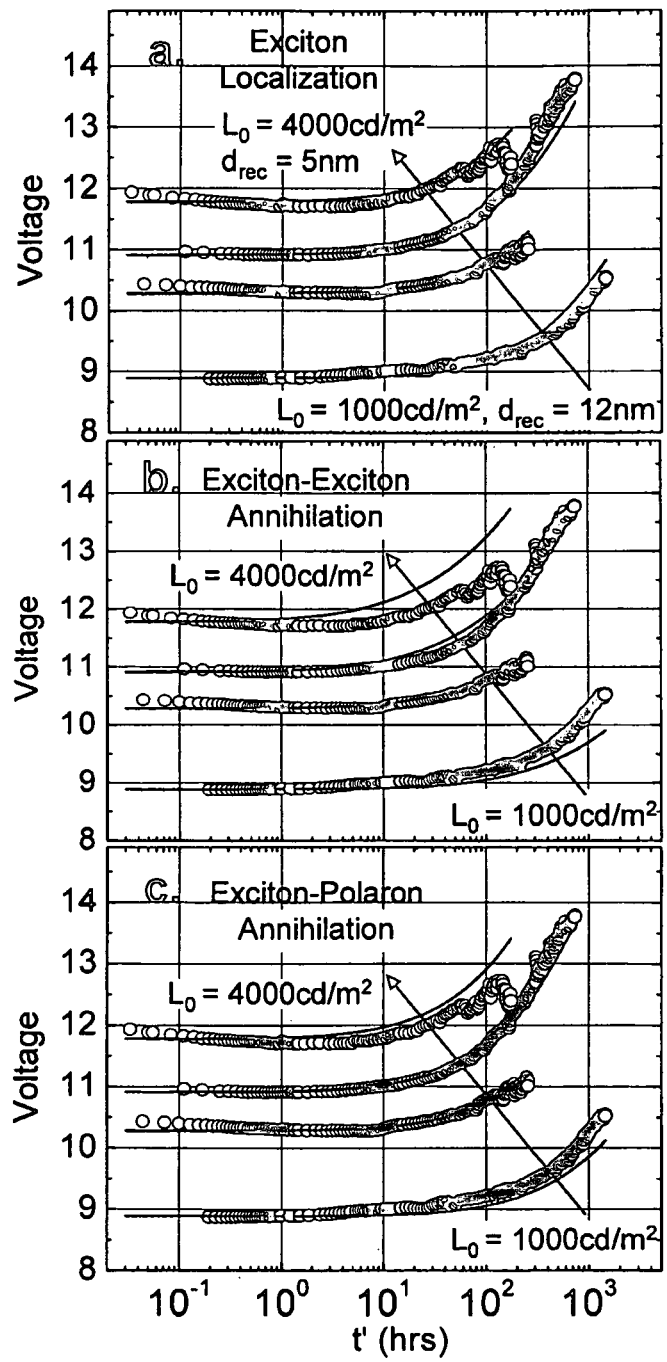
FIGS. 6A-6C.
Figure 7:
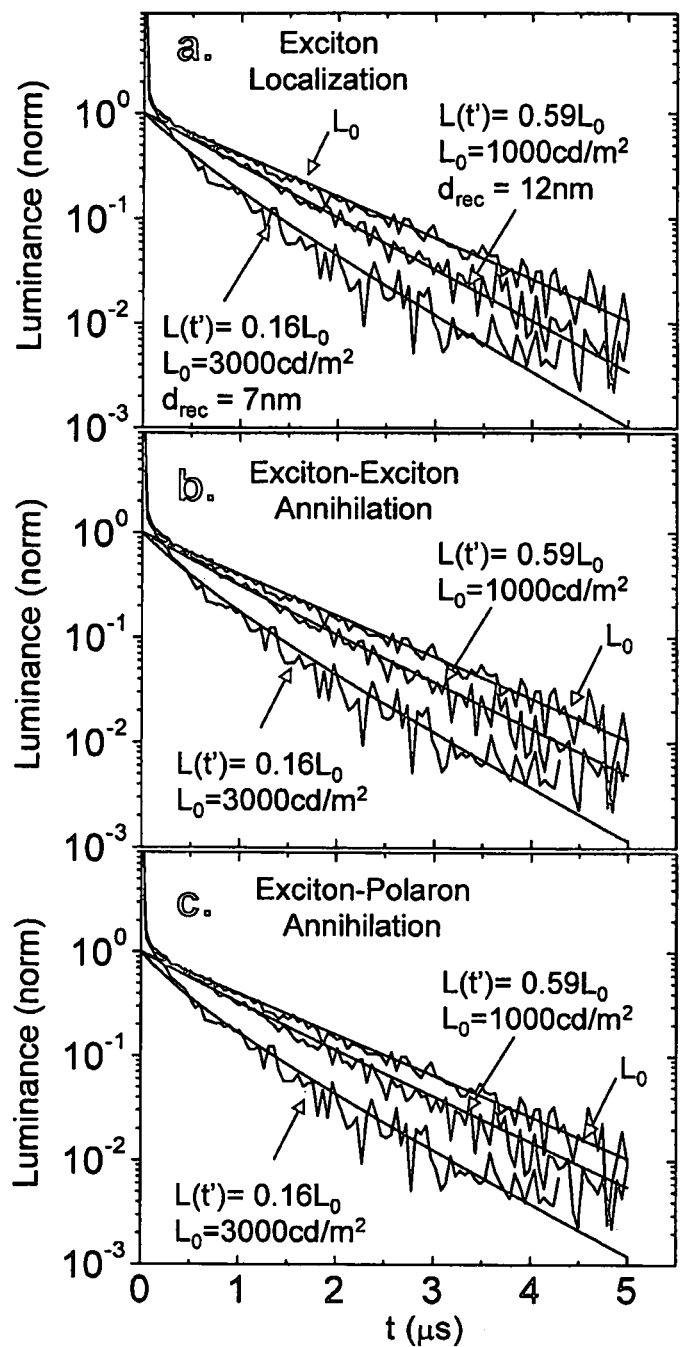
FIGS. 7A-7C.

To determine which of these processes were most active, the data in FIGS. 5-7 to the model discussed above. For each degradation model, a single set of parameters was used to fit the luminance, voltage, and PL data. The calculated luminance degradation slope following the 'knee' (i.e., onset of downward slope) of each curve (FIG. 5) depended primarily on the degradation mode assumed, while only slightly on the choice of parameter values, which determined the position of the 'knee' in time, t'. Each set of parameters is provided in Table 1, below.

TABLE 1

Model Parameter Values

|  | Parameter | Exciton | Ex-Ex | Ex-Pol |
|---|---|---|---|---|
| Variable | $d_{rec}$ (nm) | 12, 9, 7, 5, ±5 | 10 ± 3 | 8 ± 2 |
|  | $K_{DR}$ (cm³s⁻¹) | (4 ± 3) × $10^{-12}$ | (4 ± 3) × $10^{-12}$ | (5 ± 3) × $10^{-12}$ |
|  | $K_x$ (s⁻¹ or cm³s⁻¹) | (6 ± 3) × $10^{-6}$ | (1.7 ± 0.9) × $10^{-22}$ | (7 ± 2) × $10^{-24}$ |
|  | σ (cm²) | 2 × $10^{-17}$ | 3 × $10^{-17}$ | $10^{-17}$ |
|  | $E_t - E_{Fv}$ (eV) | 0.21 ± 0.05 | 0.15 ± 0.04 | 0.17 ± 0.03 |

TABLE 1-continued

Model Parameter Values

|  | Parameter | Exciton | Ex-Ex | Ex-Pol |
|---|---|---|---|---|
| Fixed, Common | $J$ (mA/cm$^2$) | 6.85 ($L_0$ = 1000 cd/m$^2$), 15.12 ($L_0$ = 2000 cd/m$^2$) | | |
| | | 24.26 ($L_0$ = 3000 cd/m$^2$), 34.36 ($L_0$ = 4000 cd/m$^2$) | | |
| | $\tau$ (μs) | 1.10 ± 0.08 | | |
| | $\mu_p$ (cm$^2$V$^{-1}$s$^{-1}$) | $2 \times 10^{-7}$ | | |
| | $\mu_n$ (cm$^2$V$^{-1}$s$^{-1}$) | $8 \times 10^{-8}$ | | |
| | $T$ (K) | 295 | | |
| | $x_1$ (nm) | 40 | | |
| | $x_2$ (nm) | 70 | | |
| | $x_3$ (nm) | 115 | | |

The exciton-polaron model provided the best fit to the data, as discussed below. Electron and hole mobilities representative of those found for a similar CBP based host-guest combination were kept constant in all fits. In FIG. 5C, the model deviated slightly in advanced stages of degradation ($L(t') < 0.4L_0$), where the data showed lower luminance than predicted. This may result from a change in charge balance due to the voltage rise FIG. 6. This resulted in higher polaron densities, and thus to an increased rate of degradation, providing a positive feedback not considered in the model.

Accordingly, each degradation mechanism was marked by its own, distinct, functional dependence. This was evident from approximate solution of Equations (1)-(3) in the limit that $Q(x,t')$ is large ($\geq 10^{17}$ cm$^{-3}$). Use of Equation (4) yielded a polynomial of different order in $Q(x,t')$ for each degradation mechanism: quadratic for single polaron localization (Equation (4a)), 4$^{th}$ order for exciton localization (Equation (4b)), 7$^{th}$ order for exciton-exciton annihilation (Equation 4(c)), and 5$^{th}$ order for exciton-polaron annihilation (Equation 4(d)). The distinguishing feature of each degradation mode was thus the order of the polynomial used to fit the data, which led to the parameter-independent functional differences in the fits of FIG. 5.

The parameters in Table 1 were consistent with expectations for this guest-host materials combination. For example, the values suggested that defect hole traps are nearly full, lying at about 0.1 eV above the hole quasi-Fermi level. Characteristic recombination lengths were all consistent with literature reported values of in the range of about 8 nm to about 12 nm. Also, the defect exciton quenching rate, $K_{DR} \sim 4 \times 10^{-12}$ cm$^3$s$^{-1}$, was similar to that reported for other bimolecular quenching reactions in OLEDs. Low capture cross-sections of about $\sigma = 10^{-17}$ cm$^{-3}$ resulted from localization of large effective mass holes that were characteristic of organic molecules.

The relative contributions to luminance loss from defect exciton quenching and non-radiative recombination were estimated to be about 70% and about 30% respectively. The existence of quenching was confirmed by the PL data of FIG. 7, and non-radiative recombination is inferred from the presence of charged defects that led to the observed voltage rise.

The average defect density, $Q_{AVG}(t') = 1/d_{rec} \int Q(x,t')dx$, was calculated using the exciton-polaron model, is shown in 9A. The increase in defect density was linear for t<10 hrs, and rolls off at longer times. From FIG. 5C and FIG. 9A, it was inferred that a defect density of about $10^{18}$ cm$^{-3}$, or about 0.1% of the molecular density leads to greater than about 50% loss in luminescence. The rates of defect formation, $F_X(t')$, corresponding to the densities in FIG. 9A, were plotted in FIG. 9B. At about 1000 cd/m$^2$, $F_X \approx 0.04$, or about 1 defect per about 25 excitons was formed every hour.

The effects of exciton-polaron annihilation on device lifetime may be reduced by increasing $d_{rec}$ and decreasing $K_X$, as shown in FIGS. 9A and 9B, respectively. These results were calculated for a device with $L_0 = 1000$ cd/m$^2$, maintaining all other parameters at the values in Table 1. The device lifetime more than doubled when recombination was uniform across the EML ($d_{rec} \to \infty$), as compared to $d_{rec} = 8$ nm found for the devices studied here. Further, for $d_{rec} > 30$ nm, there was little improvement in LT$_{80}$. Since the voltage of an OLED was strongly dependent on layer thickness, about 30 nm was thus considered a nominal upper limit to the EML thickness in practical, efficient OLEDs. Also, in FIG. 15B, a 6-fold increase of LT$_{80}$ was calculated as $K_X$ was reduced from about $7 \times 10^{-24}$ cm$^{-3}$s$^{-1}$, to about $1 \times 10^{-24}$ cm$^{-3}$s$^{-1}$.

As indicated in FIG. 8C, it was the excess energy gained by the polaron that drove the exciton-polaron degradation mechanism. It enabled direct and pre-dissociation reactions (route 1) if the repulsive potential, R, existed. However, due to the typically fast (ps) rates of vibronic relaxation from upper excited states, the hot-molecule mechanism (route 2) was perhaps even more important. In this case, vibrational dissipation of the excess electronic energy (about 2.7 eV) led to cleavage of low energy molecular bonds.

Guest triplet excitons and host polarons were likely to be the dominant participants in the exciton-polaron defect formation reactions. The guest exciton density was much higher than the density on the host, since lifetimes on the host were short (less than about 1ns) due to rapid energy transfer to the guests, where they exist as triplets for about 1 μs. Since both Förster and exchange exciton-polaron annihilation mechanisms were strongly distance dependent, the physical separation of guests discouraged guest-guest annihilations. Accordingly, it was inferred that energy exchanged by annihilation of the guest triplet exciton to the host polaron resulted in a dissociative process of the host molecule itself. The fragments were in close proximity to the guest molecule and thus quenched any subsequent triplets on that molecule, rendering it a permanent non-radiative center. Furthermore, as noted above, the fragmented molecule also acted as a deep trapping center, resulting in the observed operating voltage rise.

It is apparent that the efficiency of hot-molecule dissociation may increase with the amount of energy transferred to the polaron. Since this energy was provided by the guest, this suggested that the degradation rate ($K_x$) was a function of the guest exciton energy. In this case, red phosphorescent OLEDs would show the longest lifetimes, followed by green and then by blue devices. This has been observed in all OLED reliability studies to date in both polymer and small molecular weight systems, as well as for electrofluorscent and electrophosphorescent guest-host materials combinations. For example, the longest reliability observed in the red, green and blue Ir-based small molecule electrophosphorescent OLEDs were about $10^6$ hrs, $5\times10^4$ hrs and about $2\times10^4$ hrs, respectively. Although there were significant differences between the device structures and test conditions used in each of these studies, the lifetime scaling was clearly apparent and was consistent with our energy-based model for device degradation.

Figure 10:
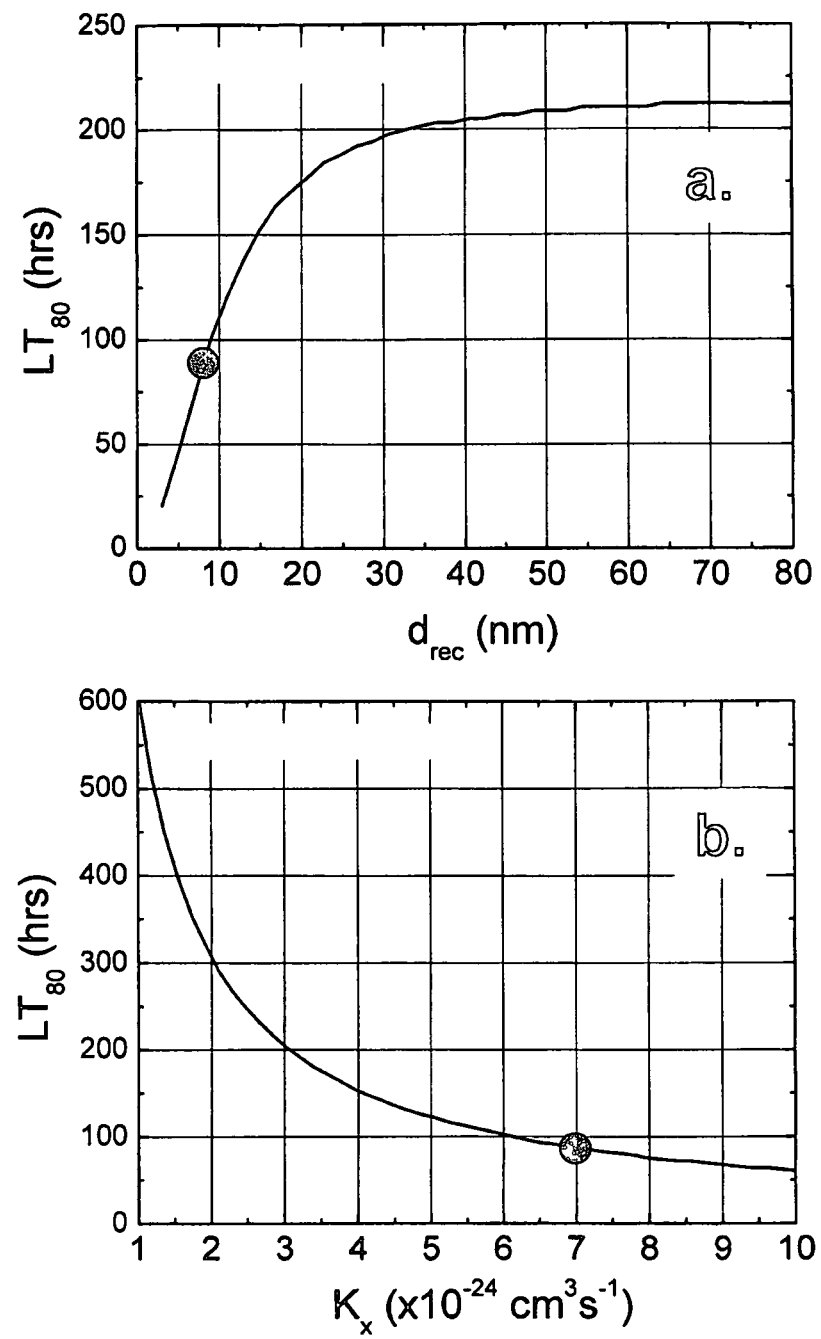
FIGS. 10A-10B.

Strategies for minimizing exciton-polaron annihilation involved lowering either $K_x$ or the densities of excitons and polarons. FIG. 10A shows the results of lowering both exciton and polaron densities by expanding the recombination zone. For example, control of electron and hole mobilities in the EML as well as the strategic placement of energy barriers in the device may lead to a more uniform and distributed recombination zone. Finally, engineering host and guest molecules to lower the annihilation probability may lead to increased lifetime (FIG. 10B) as well as improved efficiency at high brightness. Due to the distance dependence of annihilation processes, increasing the intermolecular separation through addition of steric bulk to guest and host molecules may lead to decreased $K_x$ and longer lifetimes, although this may also reduce the device efficiency by impeding exciton or charge transfer within the EML.

While the invention is described with respect to particular examples and specific embodiments, it is understood that the present invention is not limited to these examples and embodiments. For example, the phosphorescent materials may contain stereo and/or structural isomers. The invention as claimed therefore includes variations from the particular examples and specific embodiments described herein, as will be apparent to one of skill in the art.

What is claimed is:

1. An organic light emitting device, comprising:
an anode,
a cathode,
an emissive layer disposed between the anode and the cathode, the emissive layer further comprising a host and a phosphorescent emissive dopant; wherein the phosphorescent emissive dopant is selected from the group consisting of:

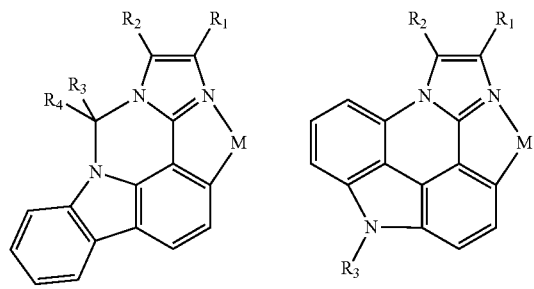

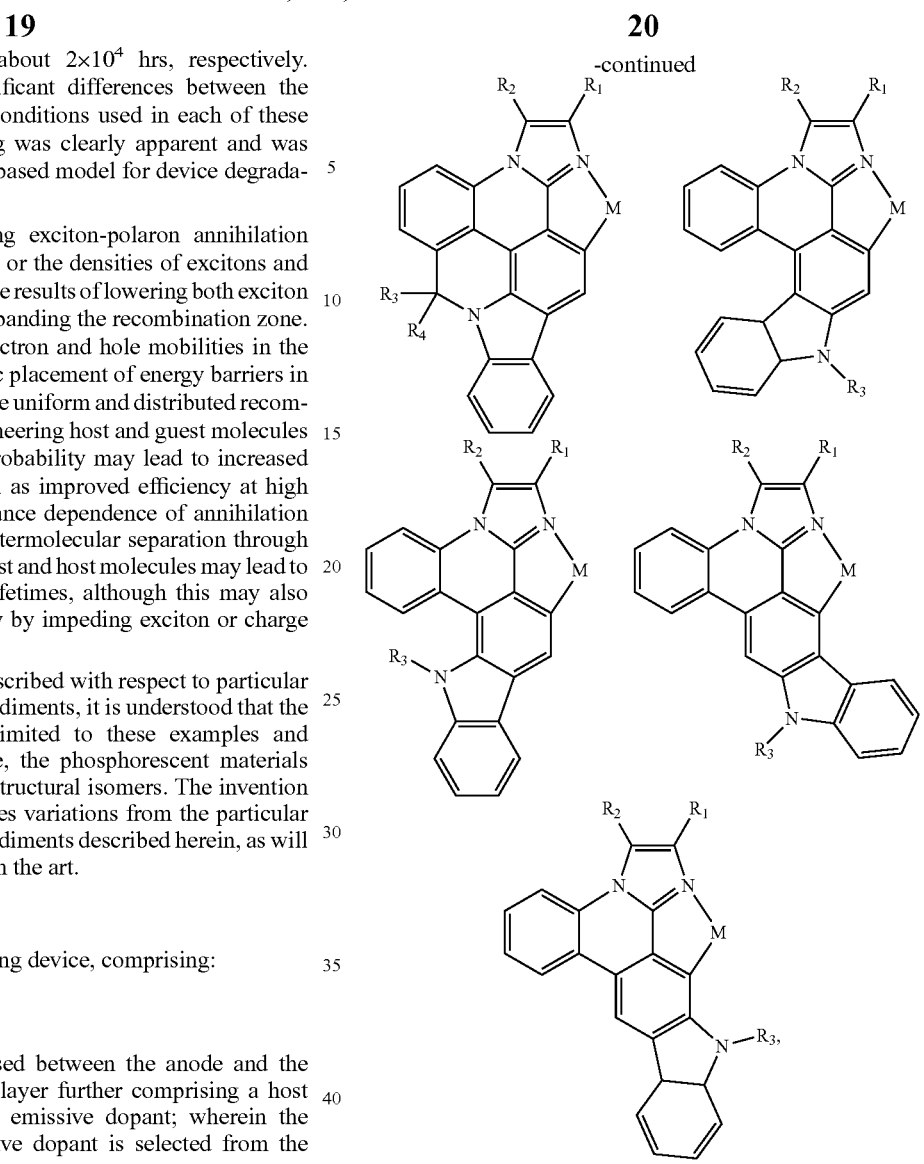

where $R_1$-$R_4$ are independently selected from the group consisting of: H, aryl and
alkyl, where the aryl and alkyl may be further substituted,
Ar is an aryl that may be further substituted, and
M is a metal having an atomic weight greater than 40.

2. The device of claim 1, wherein M is iridium.
3. The device of claim 2, wherein three identical ligands are coordinated to the metal M.
4. The device of claim 1, wherein additional ligands are coordinated to the metal M.
5. The device of claim 1, wherein the device has a graded interface.